US006991922B2

(12) United States Patent
Dupret et al.

(10) Patent No.: US 6,991,922 B2
(45) Date of Patent: *Jan. 31, 2006

(54) PROCESS FOR IN VITRO CREATION OF RECOMBINANT POLYNUCLEOTIDE SEQUENCES BY ORIENTED LIGATION

(75) Inventors: Daniel Dupret, Calvisson (FR); Fabrice Lefevre, Nîmes (FR); Jean-Michel Masson, Toulouse (FR)

(73) Assignee: Proteus S.A., Nimes (FR)

( * ) Notice: Subject to any disclaimer, the term of this patent is extended or adjusted under 35 U.S.C. 154(b) by 399 days.

This patent is subject to a terminal disclaimer.

(21) Appl. No.: 09/840,861

(22) Filed: Apr. 25, 2001

(65) Prior Publication Data

US 2003/0215800 A9    Nov. 20, 2003

Related U.S. Application Data

(63) Continuation-in-part of application No. 09/723,316, filed on Nov. 28, 2000, which is a continuation of application No. PCT/FR99/01973, filed on Aug. 11, 1999.

(30) Foreign Application Priority Data

Aug. 12, 1998  (FR)  ............................ 98 10338

(51) Int. Cl.
    *C12P 19/34*  (2006.01)
    *C12Q 1/68*   (2006.01)
(52) U.S. Cl. .................. 435/91.1; 435/6; 435/91.2
(58) Field of Classification Search .............. 435/6, 435/455, 91.2, 91.1, 5, 7.5, 91.5, 91.52; 536/23.1, 536/24.3
    See application file for complete search history.

(56) References Cited

U.S. PATENT DOCUMENTS

| 4,500,640 | A | * | 2/1985 | Katsumata et al. ..... 435/252.32 |
| 5,605,793 | A |   | 2/1997 | Stemmer |
| 5,614,389 | A | * | 3/1997 | Auerbach .................. 435/91.2 |
| 5,830,721 | A | * | 11/1998 | Stemmer et al. ............ 435/489 |
| 5,837,458 | A |   | 11/1998 | Minshull et al. |
| 6,117,679 | A | * | 9/2000 | Stemmer ..................... 435/440 |
| 6,132,970 | A |   | 10/2000 | Stemmer |
| 6,143,527 | A | * | 11/2000 | Pachuk et al. ............. 435/91.1 |
| 6,153,410 | A |   | 11/2000 | Arnold et al. |
| 6,165,793 | A |   | 12/2000 | Stemmer |

(Continued)

FOREIGN PATENT DOCUMENTS

EP    0752008    1/1997

(Continued)

OTHER PUBLICATIONS

Gary et al., "The DNA Repair Endonuclease XPG Binds to Proliferating Cell Nuclear Antigen (PCNA) and Shares Sequence Elements with the PCNA-binding Regions of FEN-1" The Journal of Biological Chemistry, 1997, vol. 39, pp. 24552-24559.*

(Continued)

*Primary Examiner*—Kenneth R. Horlick
*Assistant Examiner*—Young J. Kim
(74) *Attorney, Agent, or Firm*—Hunton & Williams LLP

(57) ABSTRACT

The object of this invention is a process for the creation of at least one recombinant polynucleotide sequence comprising a step of oriented ligation of fragments derived from a bank of at least two polynucleotide sequences, and optionally cloning the recombinant polynucleotide sequences, and the selection of polynucleotide sequences offering advantageous characteristics compared to one or several reference sequences.

44 Claims, 9 Drawing Sheets

U.S. PATENT DOCUMENTS

| | | |
|---|---|---|
| 6,171,820 B1 | 1/2001 | Short |
| 6,177,263 B1 | 1/2001 | Arnold et al. |
| 6,180,406 B1 | 1/2001 | Stemmer |
| 6,238,884 B1 | 5/2001 | Short et al. |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,322,969 B1 | 11/2001 | Stull et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,337,186 B1 | 1/2002 | Krebber |
| 6,344,356 B1 | 2/2002 | Stemmer |
| 6,348,314 B1 * | 2/2002 | Prudent et al. ............ 435/6 |
| 6,358,740 B1 | 3/2002 | Patten et al. |
| 6,361,974 B1 | 3/2002 | Short et al. |
| 6,365,377 B1 | 4/2002 | Patten et al. |
| 6,365,408 B1 | 4/2002 | Stemmer |
| 6,368,861 B1 | 4/2002 | Crameri et al. |
| 6,376,246 B1 * | 4/2002 | Crameri et al. .......... 435/440 |
| 2001/0039014 A1 | 11/2001 | Bass et al. |
| 2001/0049104 A1 * | 12/2001 | Stemer et al. ............ 435/6 |

FOREIGN PATENT DOCUMENTS

| | | |
|---|---|---|
| EP | 1138763 | 2/2002 |
| FR | 2782323 | 2/2000 |
| JP | 11075849 | 3/1999 |
| WO | WO 95/22625 | 8/1995 |
| WO | WO 97/20078 | 6/1997 |
| WO | WO 97/22715 | 6/1997 |
| WO | WO 98/15567 | 4/1998 |
| WO | WO 98/27230 | 6/1998 |
| WO | WO 98/32845 | 7/1998 |
| WO | WO 00/58517 | 10/2000 |
| WO | WO 00/77262 | 12/2000 |
| WO | WO 01/23401 | 4/2001 |
| WO | WO 01/27160 | 4/2001 |
| WO | WO 01/29211 | 4/2001 |
| WO | WO 01/29212 | 4/2001 |
| WO | WO 01/42509 | 6/2001 |
| WO | WO 01/51663 | 7/2001 |
| WO | WO 01/64864 | 9/2001 |
| WO | WO 01/70947 | 9/2001 |
| WO | WO 01/73000 | 10/2001 |
| WO | WO 01/90346 | 11/2001 |
| WO | WO 01/96551 | 12/2001 |
| WO | WO 02/04629 | 1/2002 |
| WO | WO 02/06469 | 1/2002 |

OTHER PUBLICATIONS

Coco et al., "DNA Shuffling method for generating highly recombinant genes and evolved enzymes," Nature Biotechnology, Apr. 2001, vol. 19, pp. 354-359.*

Rouwendal, et al., Simultaneous Mutagensis of Multiple Sites: Application of the Ligase Chain Reaction Using PCR Products Instead of Oligonucleotides, Biotechniques, Vo. 15, No. 1, Jul. 1993, pp. 172-178.

Stemmer, W. P. C., "DNA shuffling by random fragmentation and reassembly: In vitro recombination for molecular evolution", Proc. Natl. Acad. Sci. USA, vol. 91, pp. 10747-10751, Oct. 1994.

Punnonen, J. et al., "Molecular breeding by DNA shuffling", Science & Medicine, pp. 38-47, Mar./Apr. 2000.

Coco, W. M. et al., "DNA shuffling method for generating highly recombined genes evolved enzymes", Nature Biotechnology, vol. 15, Apr. 2001, pp. 354-358.

Pelletier, J., "A rachitt for our toolbox", Nature Biotechnology, vol. 19, No. 4, Apr. 2001, pp. 314-315.

Crameri, A. et al., "DNA shuffling of a family of genes from diverse species accelerates directed evolution", Nature, vol. 391, Jan. 1998, pp. 288-291.

Ness, J. E. et al., "DNA shuffling of subgenomic sequences of subtilisin", Nature Biotechnology, vol. 17, Sep. 1999, pp. 893-896.

Chang, C. J. et al., "Evolution of a cytokine using DNA family shuffling", Nature Biotechnology, vol. 17, Aug. 1999, pp. 793-797.

Minshull, J. et al., "Protein evolution by molecular breeding", Current Opinion in Chemical Biology, 1999, vol. 3, pp. 284-290.

Harayama, S. "Artificial evolution by DNA shuffling", Tibtech, Feb. 1998, vol. 16, pp. 76-82.

Kirtzman, A., "Advances in directed protein evolution by recursive genetic recombination: applications to therapeutic proteins", Current Opinion in Biotechnology, 2001, vol. 12, pp. 361-370.

Zhao, H. et al., "Optimizing of DNA Shuffling for High Fidelity Recombination", Nucleic Acids Research, vol. 25, No. 6, pp. 1307-1308, (1997).

Lyamichev, V. et al., "Polymorphism Identification and Quantitative Detection of Genomic DNA by Invasive Cleavage of Oligonucleotide Probes", Nature Biotechnology, vol. 17, pp. 292-296 (1999).

* cited by examiner

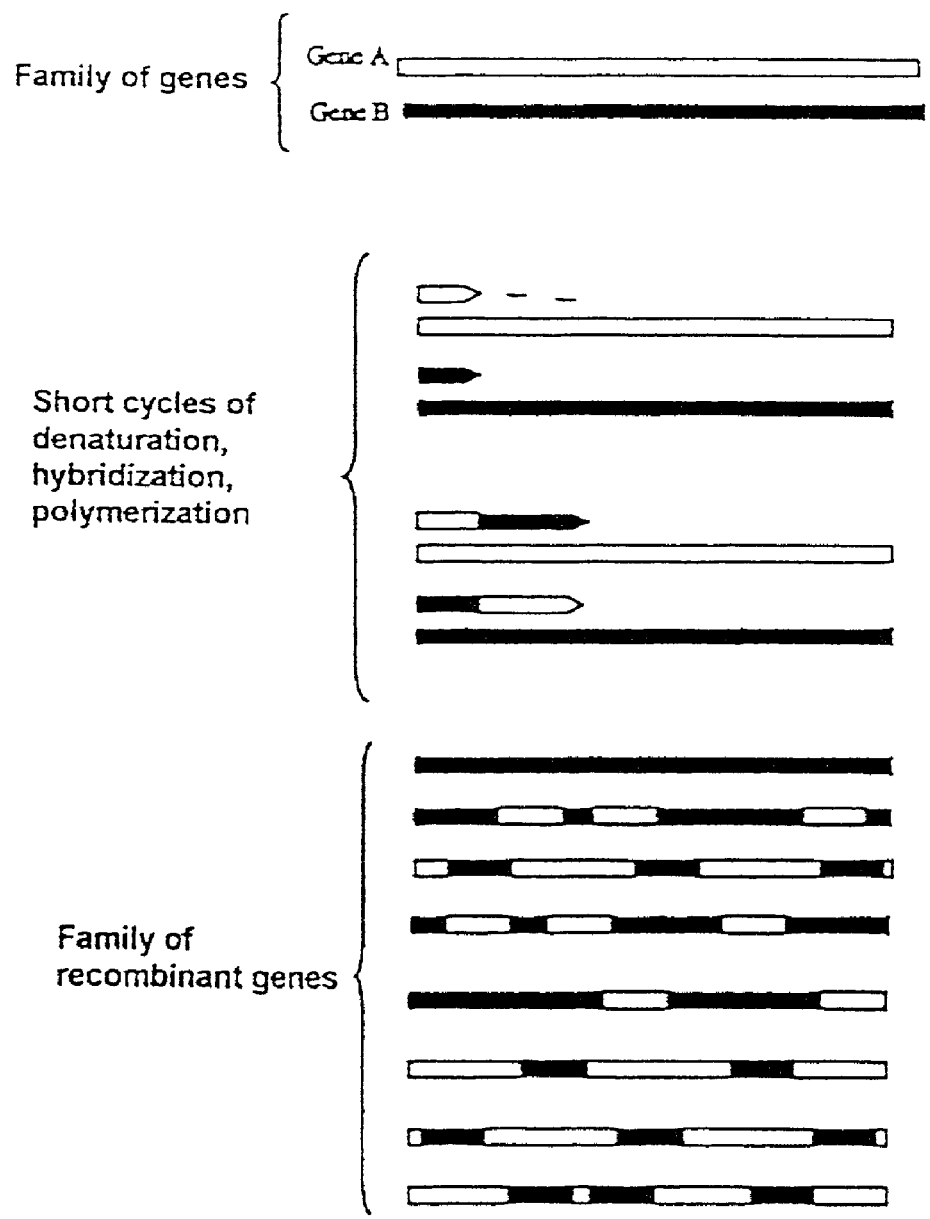

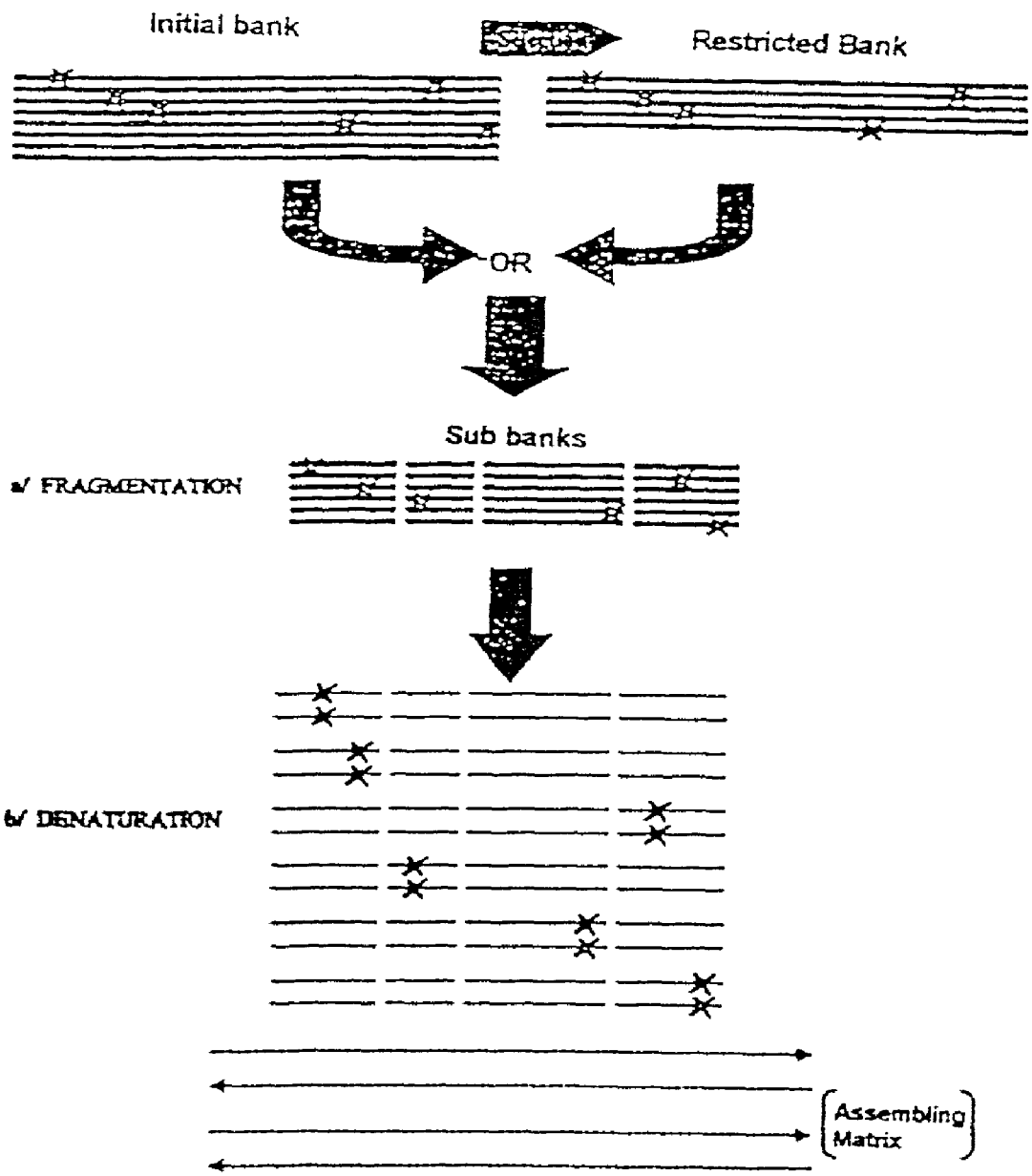

Fig. 2- continued
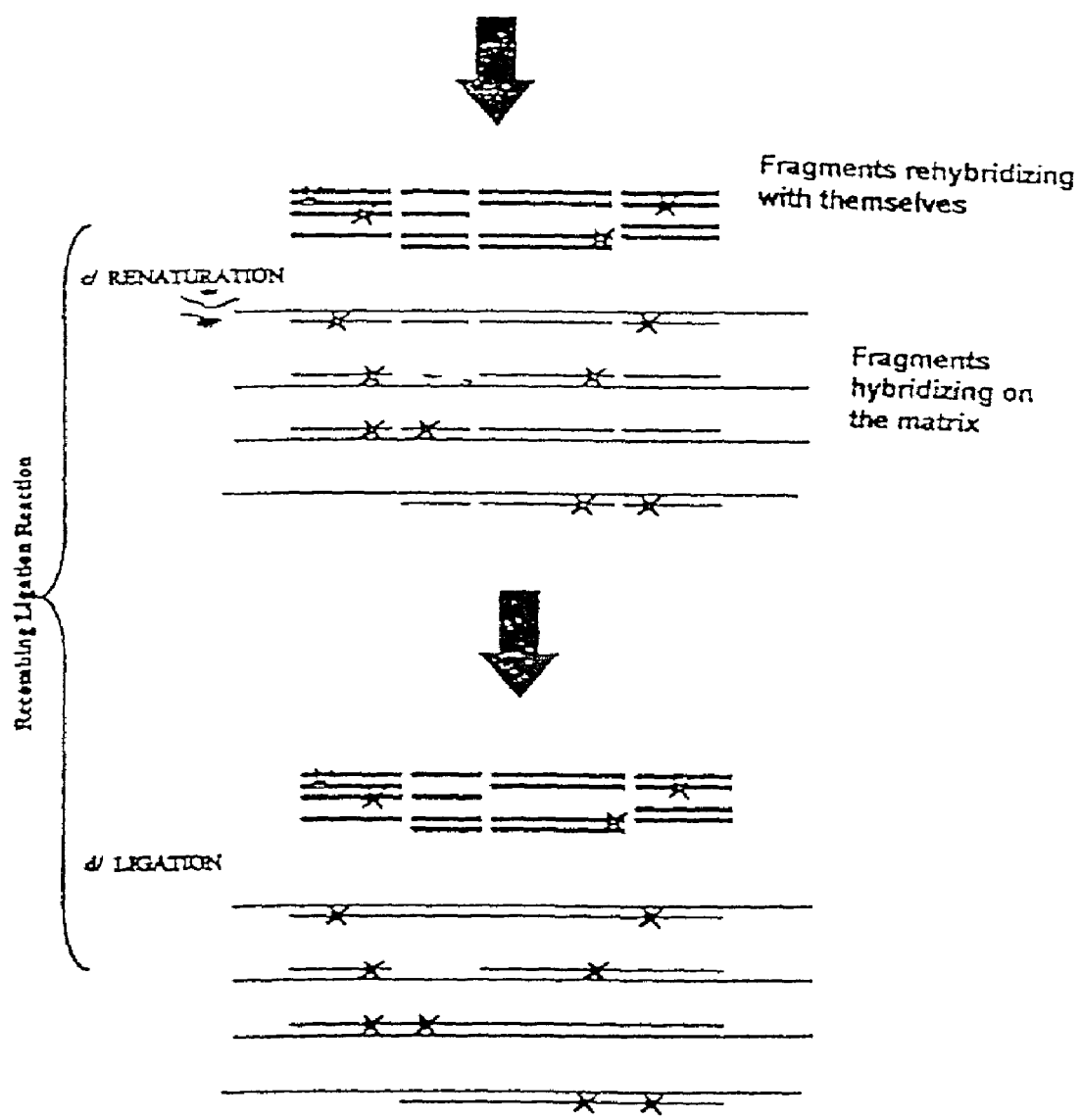

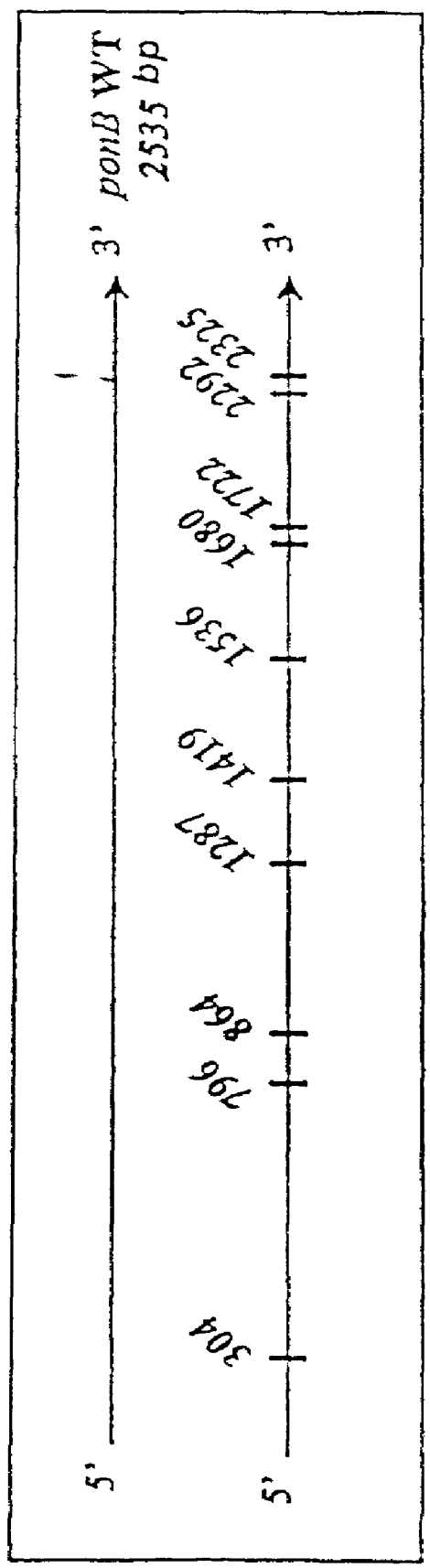
Figure 3: Position of the ten mutation zones (sites PvuII and PstI)

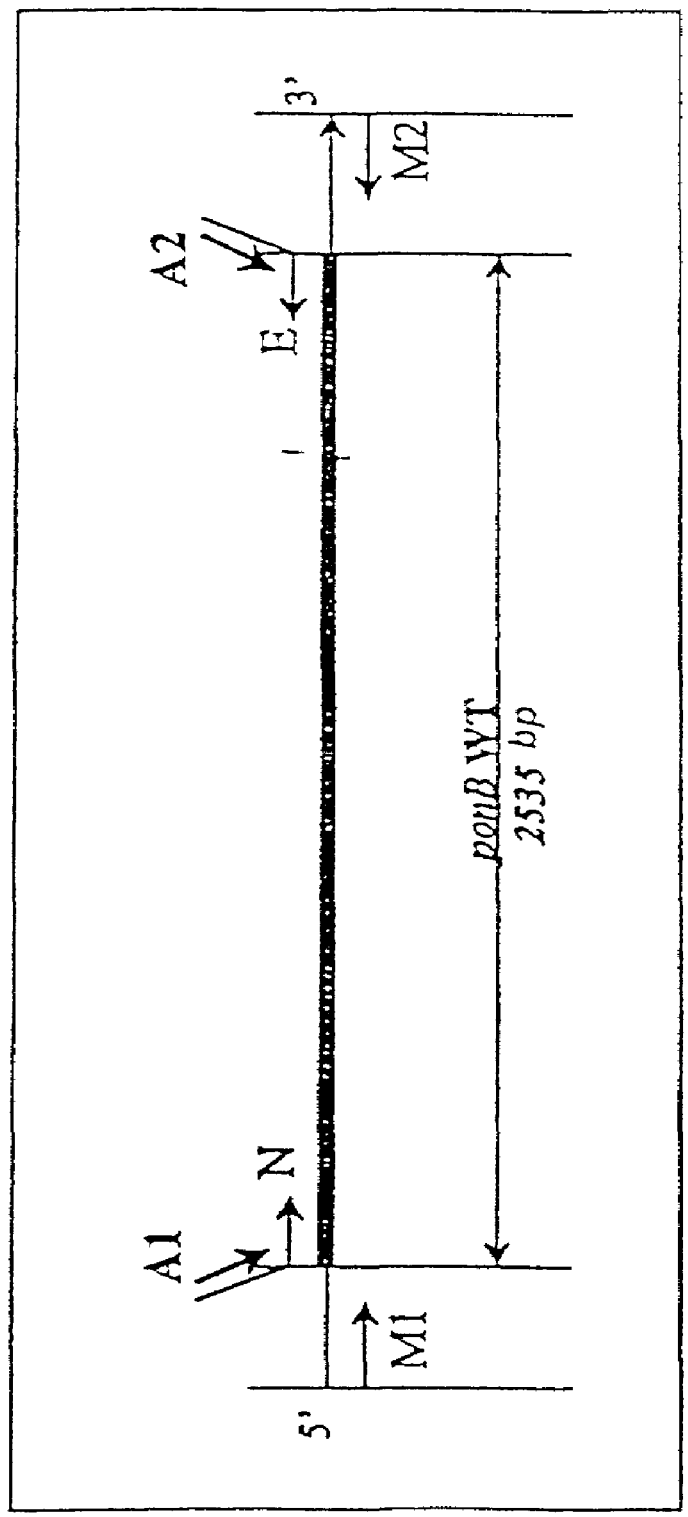
Figure 4: Position of the primers used as compared to the sequence of the ponB gene

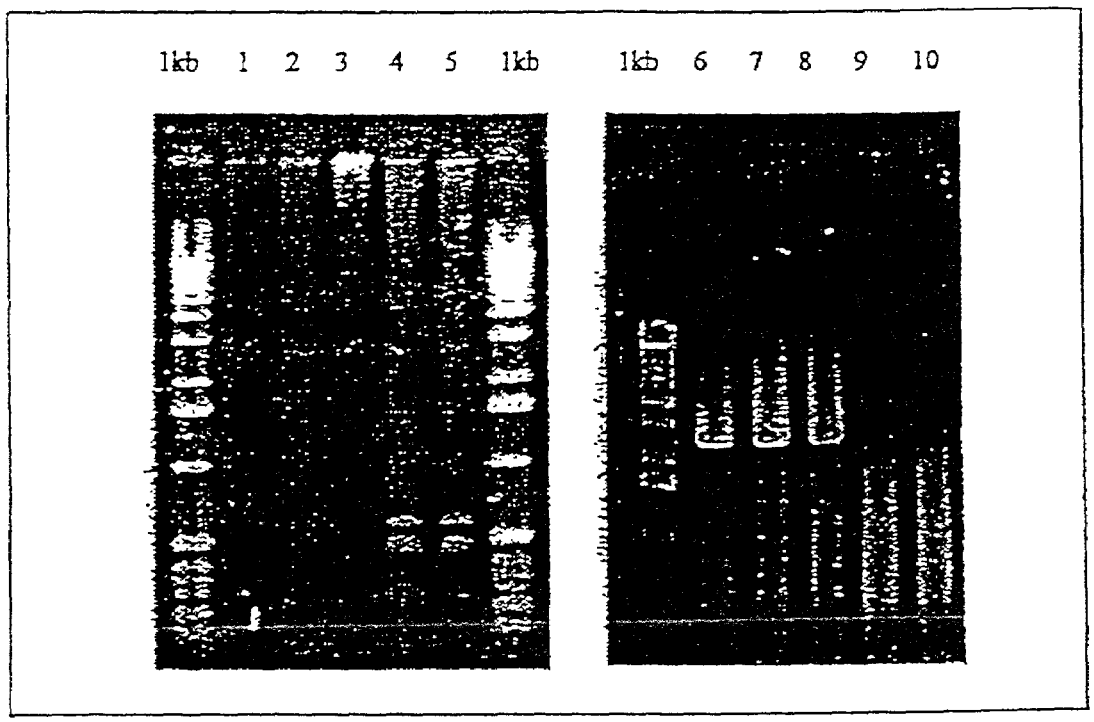
Fig. 5 : Migration of the RLR reactions and of the PCR amplifications of these reactions
Tracks:  
1/ RLR 1           6/ PCR RLR 1  
2/ RLR 2           7/ PCR RLR 2  
3/ RLR 3           8/ PCR RLR 3  
4/ RLR 4           9/ PCR RLR 4  
5/ RLR Control    10/ PCR RLR Control

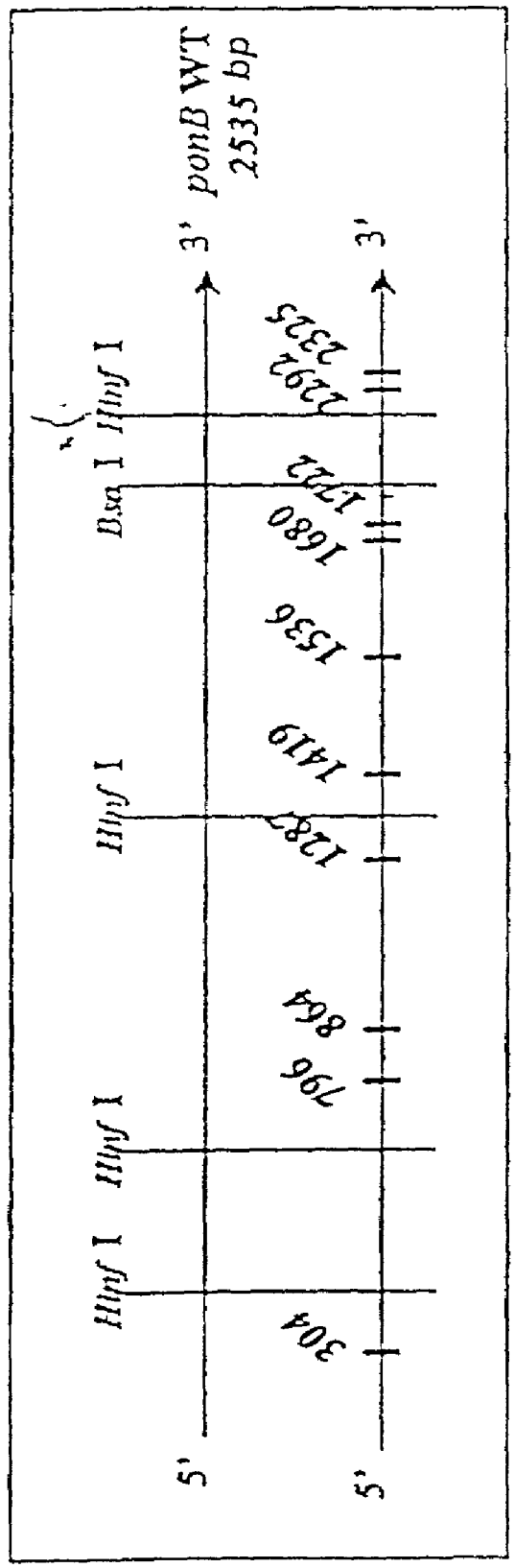
Figure 6 : Position of the mutations as compared to the restriction fragments

PROCESS FOR IN VITRO CREATION OF RECOMBINANT POLYNUCLEOTIDE SEQUENCES BY ORIENTED LIGATION

CROSS-REFERENCE TO RELATED APPLICATIONS

This application is a CIP of U.S. application Ser. No. 09/723,316, filed Nov. 28, 2000, which is a continuation of PCT Application No. PCT/FR99/01973 (WO 0009679), filed Aug. 11, 1999.

This invention relates to a method of obtaining, in vitro, recombinant polynucleotide sequences by oriented ligation. The invention aims in particular at creating, then selecting, polynucleotide sequences able to offer one or several advantageous properties compared to corresponding properties of reference sequences and thus able to provide an improved phenotype and/or to produce improved proteins.

Reference sequence is understood as a sequence having properties close to those being sought.

In vitro is understood as any event, reaction, or process that does not take place in a living organism.

Ligation is understood as a process that allows the creation of a phosphodiester bond between two nucleic acid fragments.

Oriented ligation is understood as any process of ligation that makes it possible to assemble nucleic acid molecules in a set order, notably by hybridization of said nucleic acid molecules on at least one nucleotide matrix.

Polynucleotide sequence is understood as any single- or double-stranded nucleic acid molecule.

Various techniques have been developed to promote in vitro recombination among different polynucleotide sequences, among them can be cited, in particular, DNA shuffling and StEP, both based on the use of PCR.

DNA shuffling comprises two steps, the random fragmentation of polynucleotide sequences by DNAase I and amplification by PCR, in which the previously created fragments act as initiators. At each hybridization step, the change of matrix causes recombinations at regions having homologous sequences. StEP consists in mixing various polynucleotide sequences containing various mutations in the presence of a pair of initiators. This mixture is subjected to a PCR reaction in which the hybridization and polymerization steps are consolidated into a single, very brief step. These conditions make it possible to hybridize the initiators but reduce the polymerization speed so that the fragments that are partially synthesized hybridize randomly on the polynucleotide sequences carrying the various mutations, thus making the recombination possible. In each of these two methods, the polymerization step is indispensable to the recombination process. Thus, depending on the polymerases selected, this polymerization step can produce undesired supplementary mutations. Further, after a certain number of cycles, DNA shuffling and StEP are based on the principle of hybridization of a "mega-initiator" on a matrix, which probably causes difficulties in implementation for polynucleotide sequences whose size is greater than 1.5 Kpb. Finally, these two techniques do not allow the rate of recombinations to be controlled, since the latter occur randomly during the successive stages of polymerization.

This invention aims specifically at reducing the above drawbacks by offering a simple preparation method for at least one recombinant polynucleotide sequence by using a process of oriented ligation of fragments obtained from a bank of polynucleotide sequences.

Bank of polynucleotide sequences is understood as a group of polynucleotide sequences containing at least two heterologous polynucleotide sequences.

In one embodiment of the invention, this object is achieved thanks to a process comprising the following steps:
 a) fragmentation of a bank of polynucleotide sequences,
 b) denaturation of the fragments thus obtained,
 c) hybridization of fragments obtained in step (b) with one or several assembly matrix (matrices),
 d) oriented ligation of said fragments to obtain at least one recombinant polynucleotide sequence.

When the assembly matrix is double-stranded, it is first denatured before step (c) such as, for example, during step (b).

The process of the invention makes it possible randomly to recombine various fragments within a polynucleotide sequence during steps (b), (c) and (d). This process thus reproduces, in vitro, the recombination phenomena that can occur in vivo by promoting them. The process of the invention is thus most particularly useful for recombining polynucleotide sequences among themselves to be able to create new polynucleotide sequences.

These recombinant polynucleotide sequences are able to offer advantageous properties compared to corresponding properties of references sequences and are thus able to provide an improved phenotype and/or to produce improved proteins.

This object is achieved thanks to a process comprising the following steps:
 a) fragmentation of a bank of polynucleotide sequences,
 b) denaturation of the fragments,
 c) hybridization of fragments obtained in step (b) with one or several assembly matrix (matrices),
 d) oriented ligation of said fragments to obtain at least one recombinant polynucleotide sequence,
 e) selection of recombinant polynucleotide sequences offering advantageous properties compared to corresponding properties of one or several references sequences.

The assembly matrix (matrices) can be single- or double-stranded. If one of these matrices is double-stranded, it is first denatured to be added in a single-stranded form to step (c), for example, during step (b).

The process of the invention can comprise, at the end of step (e), the repetition of steps (a), (b), (c), and (d). In this case, the bank of polynucleotide sequences contains at least one recombinant polynucleotide sequence that was selected in (e).

The process of the invention can also comprise, at the end of step (d) and before step (e), the repetition of steps (b), (c), and (d), or of steps (a), (b), (c), and (d).

This last embodiment is particularly useful if, at the end of step (e), all the fragments are not ligated. In that case, the process of the invention also comprises, at the end of step (d) and before step (e), one or several of the following reaction cycles:
 denaturation of ligated and non-ligated fragments from step (d), optionally in the presence of one or several assembly matrix (matrices),
 hybridization of said fragments with one or several assembly matrix (matrices) if the latter is (are) not present during the denaturation,
 ligation of said fragments.

These reactions of denaturation, hybridization and ligation are equivalent to steps (b), (c), and (d) but are performed not with fragments of step (a) but with ligated and nonligated fragments from step (d).

According to a particular embodiment of the process, the polynucleotide sequences of the bank are single-stranded. The use of single-stranded DNA fragments is particularly adapted to the recombination of gene families for which a given single-stranded matrix or a mix of various single-stranded matrices will be hybridized with single-stranded fragments coming from a bank of homologous genes. Since there are no strictly complementary sequences among them in the fragment population, the hybridization will not be biased toward wild sequences among the fragments or among matrix fragments. The hybridization temperature can thus be adjusted depending on how homologous the sequences are, thus producing recombinant molecules with the greatest possible degree of recombination. Banks of recombinant molecules are thus created, with higher value in terms of diversity, considerably increasing the chances of finding the good mutant at the end of the minimum recombination cycles.

To obtain single-stranded DNA molecules, a Bluescript phagemide or a vector of the family of filamentous phages such as M13mp18 can be used. Another method consists in creating double-stranded molecules by PCR by using an initiator phosphorylated at 5' and the other non-phosphorylated. The digestion of the lambda phage by the exonuclease will destroy the strands of DNA phosphorylated at 5, leaving the non-phosphorylated strands intact. Another method of creating single-stranded molecules consists in making an amplification, by asymmetric PCR, starting from a methylated DNA matrix.

Digestion by Dpn I will destroy the methylated strands, leaving intact the amplification products that will then be able to be purified after denaturation.

The process of the invention can further comprise one or several of the following steps:
- separation of recombinant polynucleotide sequences from the assembly matrix (matrices) before step (e),
- amplification of recombinant polynucleotide sequences before step (e),
- cloning of recombinant polynucleotide sequences optionally after separation of the recombinant strands from the matrix (matrices).

In one advantageous embodiment of the method, the ends of the fragments created at step (a) are such that there can be adjacent hybridization of these ends at least with one assembly matrix in step (c) and ligation of these fragments with one another at step (d). The polynucleotide sequences of the bank on which the process of the invention is performed must be such that the fragments obtained during the process have ends like those described above. These fragments can be obtained notably during step (a) or during step (d) by ligation of the fragments.

On advantageous embodiment of the process of the invention consists in simultaneously performing steps (c) and (d) as a so-called RLR reaction, in the English expression "recombining ligation reaction."

Besides the previously indicated advantages, the process of the invention is remarkable in that it promotes and accelerates the random in vitro recombination of polynucleotide sequences, these polynucleotide sequences being able to be genes. Gene is understood to be a fragment or a DNA sequence associated with a biological function. A gene can be obtained in different ways, among them chemical synthesis, synthesis by polymerization or extraction of said gene from a nucleic acid source.

The in vitro recombination of polynucleotide sequences from the initial bank by the process of the invention thus makes it possible to obtain a new bank containing sequences having acquired one or several characteristics of the sequences of the preceding bank. The process of the invention thus constitutes a technique for in vitro evolution.

The process of the invention constitutes an alternative to recombinant PCR such as the use of the techniques of DNA shuffling or StEP, since it does not require the in vitro polymerization step to achieve recombination. On the contrary, the key step in the process of the invention is step (d) of ligation on an assembly matrix (or oriented ligation), which guarantees a very high degree of fidelity during the recombination events.

The process of the invention is remarkable in that it makes it possible considerably to increase the efficiency of reassembling the fragments to be ligated by using oriented ligation. In fact, in the case of a sequence cut into n fragments, there are very numerous possibilities of reassociation of the fragments using a conventional ligation process (without using a reassembly matrix that orients the ligation), among which only one form is useful. In the process according to the invention, the ligation is oriented by the assembly matrix, which makes it possible to obtain the only useful form directly.

The fragmentation of these polynucleotide sequences in step (a) can be performed in a controlled manner or in a random manner.

If fragmentation is performed in a controlled manner, the fragmentation makes it possible precisely to control the degree of recombination desired and the position of the recombination points. According to a preferred embodiment of the process of the invention, step (a) consists in subjecting the polynucleotide sequences of the bank to hydrolysis by the action of one or several restriction enzymes. Thus, in a particular embodiment of the process of the invention, the degree of recombination and the position of the recombination points of the recombinant polynucleotide sequences are determined by the fragmentation of step (a).

Thus the greater the number of fragments produced per sequence, the greater the number of fragments necessary to recompose a sequence, which causes an increased rate of recombination. Further, the nature and the position of the ends of the fragments produced in the embodiment of the process of the invention can be known and controlled, which makes it possible to:
- precisely control the zones in which the recombination takes place, or
- to induce recombination among polynucleotide sequences, for example genes, if the ends of the fragments are created in zones that are homologous among these sequences, or in homologous zones between these sequences and the assembly matrices.

If the fragmentation is random, any enzymatic or mechanical means known to one skilled in the art and able randomly to cut the DNA can be used such as, for example, digestion by DNAase I or ultrasonication.

The process of the invention makes it possible considerably to increase the efficiency of reassembling the fragments to be ligated, it can thus be applied to the orientation of multimolecular ligation for flush ends. In this application, single- or double-stranded oligonucleotides that are exactly complementary to end 3' of a fragment and 5' of the adjacent fragment are used as the assembly matrix for steps (b) or (c), which makes possible the adjacent hybridization of these two ends on the same matrix after the denaturation step. Once hybridized, the ends of the fragments can be ligated among themselves so as to orient the ligation direction of the fragments at flush ends. The same approach can be envisaged for the orientation of the ligation of fragments at cohesive ends.

A rather preferred embodiment of the process of the invention consists in adding enzymes to step (c) and/or to step (d) that are able to recognize and degrade and/or cut in a specific way the nonhybridized ends of fragments when the latter cover other hybridized fragments on the same matrix. A preferred example of this type of enzyme is the enzyme Flap endonuclease.

A particular embodiment of the process of the invention thus consists in using enzymes of the Flap endonuclease type when the fragments produced in step (a) can be covered during hybridization on the assembly matrix at step (c).

Thus, during the hybridization of DNA fragments on a matrix, these enzymes are characterized by the ability to recognize and to cut in a specific way the nonhybridized ends of these fragments when the latter cover other hybridized fragments on the same matrix.

When the fragments used during the process of the invention are double-stranded, a particular embodiment of the invention consists in using specific, single-stranded enzymes of the exonuclease type. These enzymes will be characterized by being able to recognize and to degrade in a specific way the single-stranded, nonhybridized ends of these fragments when the latter cover other hybridized fragments on the same matrix.

During step (c), hybridization, the use of this type of enzyme (notably Flap, or a single-stranded specific exonuclease) thus makes it possible to increase the number of adjacent ends able to be ligated in step (d), which is particularly significant if the fragments are obtained by random cutting, because these fragments have zones where they cover one another when they are hybridized on the assembly matrix.

In a particular embodiment of the process of the invention using an active, preferably thermostable ligase at high temperature at step (d), the enzymes able to recognize and/or to cut in a specific way the nonhybridized ends of the fragments, added at step (c) and/or at step (d), will have the same characteristics of thermoresistance and high-temperature activity as said ligase.

The bank of polynucleotide sequences on which the process of the invention is performed can be produced by any method known to one skilled in the art, for example starting from a wild-type gene, by successively managed stages of mutagenesis, by "error prone" PCR (2), by random, chemical mutagenesis, by random mutagenesis in vivo, or by combining genes of close or distinct families within the same species or different species so as to make available in said bank a variety of polynucleotide sequences.

Among these techniques, the invention envisions most particularly a process in which the bank of polynucleotide sequences is obtained by a chain polymerization reaction performed under conditions that make it possible to create random, localized mutations.

The initial bank of polynucleotide sequences can consist of synthetic sequences that will be fragmented at step (a) or that can constitute the fragments of step (a).

According to a preferred embodiment of the process of the invention, step (a) consists in subjecting the polynucleotide sequences of the bank to hydrolysis by the action of one or several restriction enzymes.

To increase the degree of recombination produced by the process of the invention, it suffices to increase the number of restriction fragments by using restriction enzymes having a large number of cutting sites on the polynucleotide sequences of the bank, or by combining several restriction enzymes. If a thermostable and thermoactive ligase is used, the size of the smallest fragment thus produced will advantageously be greater than or equal to 40 b or 40 pb, so as to maintain a hybridization temperature compatible with that of ligation step (d), which is generally on the order of 65° C.

Step (a) can further be done by producing a fragment bank by random enzymatic or mechanical treatment. In particular, step (a) can consist of a random treatment with DNAase I of a bank of polynucleotide sequences. If random enzymatic or mechanical fragmentation is used at step (a), this embodiment of the process of the invention is characterized in that it makes it possible to use fragments produced by this treatment as matrices for one another, for hybridization during step (c) or during the RLR reaction of steps (c) and (d) simultaneously.

Step (b) can be performed by combining at least two banks of distinct fragments produced separately in step (a) starting from the same initial bank by different treatments, such as, e.g., with different restriction enzymes. If such banks are used, the fragments obtained at step (a) are used as matrices for one another, for hybridization during step (c) or during the RLR reaction of steps (c) and (d) simultaneously.

The fragments of step (a) of the process of the invention can also be produced by amplification reactions (such as PCR) performed on the polynucleotide sequences of the bank. Two solutions in particular can be envisaged. In a first case, the initiated oligonucleotides can be designed so as to produce fragments whose ends are adjacent all along the assembly sequence. In a second case, the initiated oligonucleotides are designed so as to produce fragments having sequences in common, these fragments being able to act as an assembly matrix for one another at step (b) or at step (c).

The recombination efficiency of the process of the invention depends on the number of fragments produced per polynucleotide sequences at step (a). As a result, the process of the invention will use polynucleotide sequences that have been fragmented into n fragments, n advantageously being greater than or equal to 3.

The assembly matrix of step (b) or (c) is, for example, a polynucleotide sequence produced from the initial bank or a sequence contained in said bank, single- or double-stranded. If the assembly matrix (matrices) is (are) incorporated directly at step (c) of the invention, this matrix must be in the single-stranded form.

According to a variant of the process of the invention, the assembly matrices of step (b) or (c) consist of single- or double-stranded oligonucleotides.

According to a particular form of the embodiment of the process of the invention, single- or double-stranded oligonucleotides of variable length are added at step (b) or (c) in addition to the matrix. These oligonucleotides are designed to be able to substitute for some of the fragments at step (c), in fact, their sequence is such that:

if they are perfectly homologous with the sequence of the fragment they are replacing, they promote certain combinations, or if they are partially heterologous with the sequence of the fragment they are replacing, they introduce one or more supplementary, direct mutations.

Heterologous sequences are understood as two sequences whose base composition differs by at least one base.

Before step (e) of the invention, it is possible to separate the recombinant polynucleotide sequences from the assembly matrix thanks to a marker present on the assembly matrix or on the recombinant polynucleotide sequences. It is in fact possible to mark each strand of the matrix according to techniques known to one skilled in the art. For example, the marker of the assembly matrix can be a hapten and the recombinant polynucleotide sequences are separated from the assembly matrix by techniques known to one skilled in the art, such as, for example, an antihapten antibody fixed on a carrier or a biotin-streptavidin reaction, if the hapten is a biotin marker.

Other techniques can be used to separate the recombinant polynucleotide sequences from the assembly matrix. The assembly matrix can also be prepared specifically so as to facilitate its elimination at the end of the process of the invention. It can thus be synthesized by PCR amplification using methylated dATP, which makes it possible to degrade it by the restriction endonuclease Dpn I. In this case, the recombinant polynucleotide sequences must not contain methylated dATP. The matrix can also have been prepared by PCR amplification by using some dUTP, which makes it possible to degrade it by treatment with a uracil-DNA-glycosylase. Conversely, it is possible to protect the recombinant polynucleotide sequences by amplifying them by selective PCR with oligonucleotides carrying phosphorothioated groups at 5'. A treatment with an exonuclease thus makes it possible specifically to degrade the assembly matrix.

The process of the invention can comprise, before the optional cloning at step (e), a step to amplify the recombinant polynucleotide sequences. Any amplification technique is acceptable, notably PCR amplification. One of the simplest consists in performing a PCR, which makes it possible to amplify specifically the recombinant polynucleotide sequences thanks to initiators that cannot be hybridized except at the ends of recombined sequences. The PCR products are then cloned, to be characterized, and the polynucleotide sequences with advantageous characteristics compared to corresponding characteristics of reference sequences are selected.

The object of the invention is to produce polynucleotide sequences able to offer advantageous characteristics compared to corresponding characteristics of reference sequences. The recombinant polynucleotide sequences obtained at step (d) and optionally cloned are screened by any appropriate means to select the recombinant polynucleotide sequences or clones having advantageous characteristics compared with corresponding characteristics of reference sequences. Advantageous characteristics, for example, are understood to be thermostability of an enzyme or its ability to be able to function under pH or temperature conditions or saline concentrations better adapted to an enzymatic process than the reference proteins usually used for said process. By way of example of such a process, an industrial process of desizing textile fibers or bleaching of paper pulps or the production of flavors in the dairy industry, processes of biocatalysis to enzymatically synthesize new therapeutic molecules, etc., can be mentioned.

According to an advantageous embodiment of the process of the invention, the polynucleotide sequence bank can thus result from a screening having made it possible to select by any appropriate means the polynucleotide sequences offering advantageous characteristics compared to the reference sequences. The sequences thus selected constitute a restricted bank.

But it is also possible to start from a nonrestricted bank so as to maintain the representative nature of the characteristics the bank contains.

The sequences coding for the protein(s) having one or more advantageous characteristics compared to reference proteins are thus selected by in vivo or in vitro screens and can be used to form a new bank for an optional repeat of the process of the invention. An advantageous embodiment of the process of the invention thus consists in using, as a bank, several polynucleotide sequences selected after a first running of the process of the invention, optionally mixed with other polynucleotide sequences. Among the screening techniques that can be applied to each clone of step (e), screening techniques by in vitro expression using notably in vitro transcription of recombinant polynucleotide sequences, then in vitro translation of the mRNAs obtained offer the advantage of eliminating cellular physiological problems and all the drawbacks connected with in vivo expression cloning. Further, this type of screening is easily automated, which makes it possible to screen a high number of recombinant polynucleotide sequences.

The invention also relates to a recombinant polynucleotide sequence obtained by a process according to the invention, as well as a vector containing such a recombinant polynucleotide sequence, a cellular host transformed by a recombinant polynucleotide sequence or a vector of the invention, as well as a protein coded by this recombinant polynucleotide sequence. The invention also comprises the corresponding banks of recombinant polynucleotide sequences, vectors, cellular hosts or proteins.

BRIEF DESCRIPTION OF THE FIGURES

FIG. 3 represents the positions of the ten zones of mutations (Pvu II and Pst I) carried by each mutant of the ponB gene used for the examples of the implementation of the invention.

FIG. 4 represents the position of the primers used as compared to the sequence of the ponB gene.

FIG. 5 represents the migration on agarose gel of RLR and of PCR reaction products of these RLR reactions.

FIG. 6 represents the position of the mutations as compared to the restriction fragments.

EXAMPLE

Figure 1:
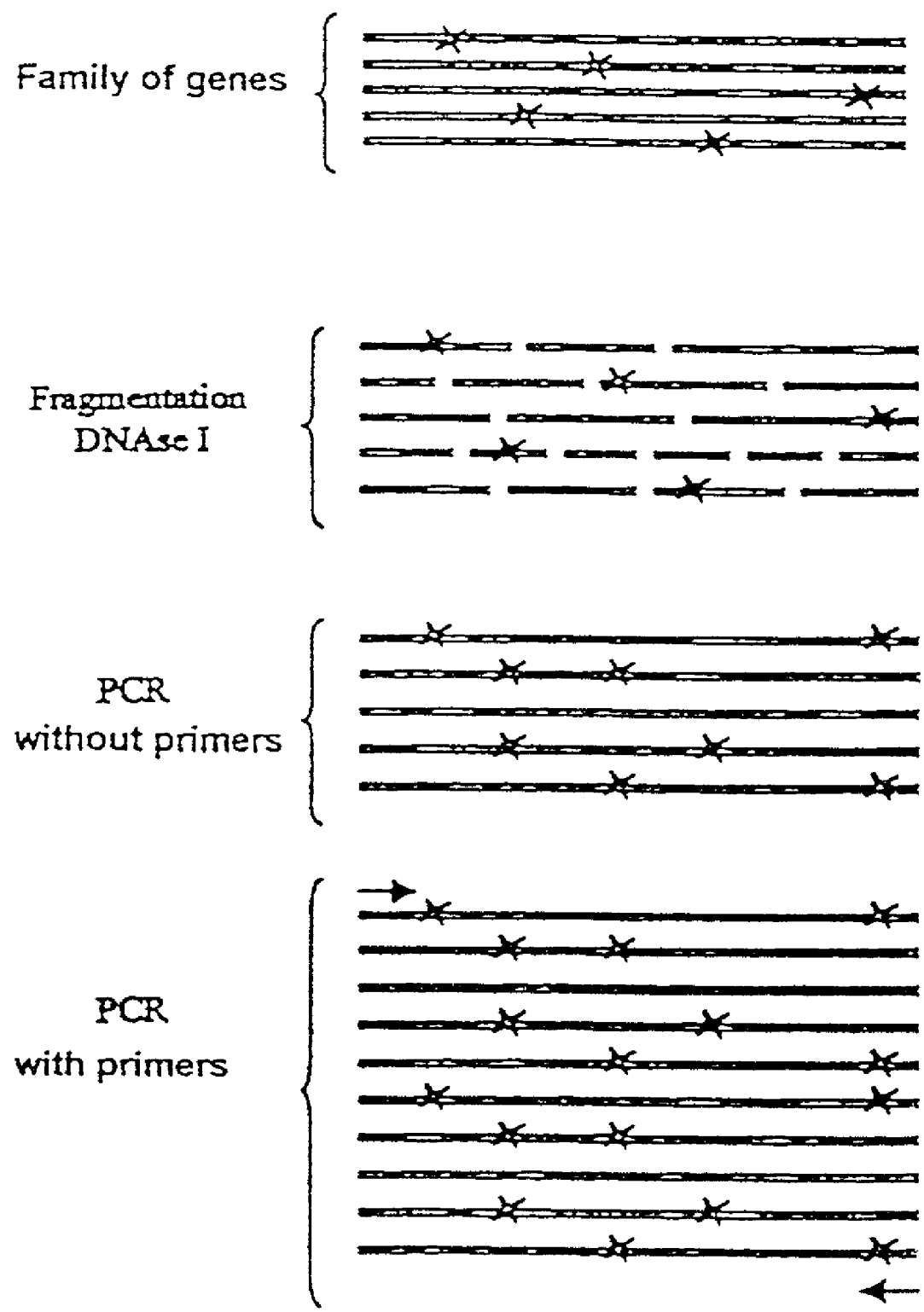
FIG. 1 is a schematic representation of the processes of the prior art corresponding respectively to DNA-shuffling (FIG. 1A) and to StEP (FIG. 1B).
Figure 2:
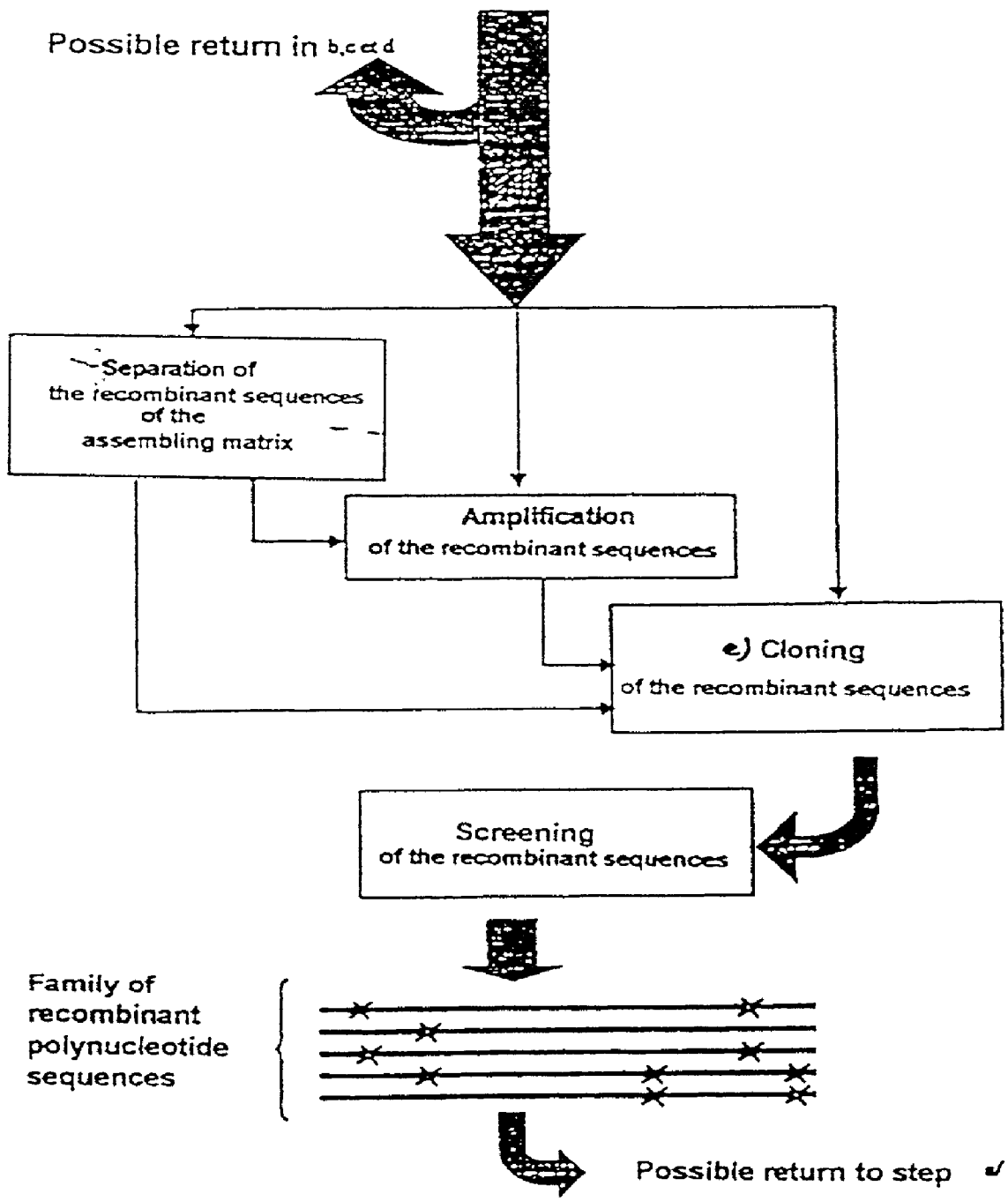
FIG. 2 is a schematic representation of an example of carrying out the process of the invention and of certain of its variations and applications.

The object of this example is to produce recombinant polynucleotide sequences from the resistance gene to kanamycin by using oriented ligation of single-stranded fragments.

First, the resistance gene to kanamycin (1 Kb) of pACYC184 is cloned in the polylinker of M13 mp18 so that the single-stranded phagemide contains the noncoding strand of the gene.

In parallel, this gene is amplified by PCR mutagenesis (error prone PCR) with two initiators that are complementary to vector sequence M13 mp18 on each side of the gene sequence. The initiator for the noncoding strand is phosphorylated while the initiator for the coding strand is not. The product of the PCR mutagenesis is digested by the lambda exonuclease, which produces a bank of coding strands for mutants of the resistance gene to kanamycin.

This bank of single-stranded molecules is digested by a mixture of restriction enzymes, notably Hae III, Hinf I and Taq I.

This bank of single-stranded fragments thus obtained is then hybridized with the single-stranded phagemide and ligated with a thermostable ligase. This step is repeated several times until the small fragments can no longer be observed during deposition on an agarose gel while the band corresponding to the single strand of the complete gene of resistance to kanamycin becomes a major component of the "smear" of single-stranded molecules visible on the gel.

The band corresponding to the size of the gene is then cut from the gel and purified. It is then hybridized with two complementary oligonucleotides (40 mer) of the M13 mp18 sequences on each side of the gene and this partial duplex is digested by Eco RI and Sph I, then ligated in an M13 mp18 vector digested by the same enzymes.

The cells transformed with the ligation product are screened for increased resistance to kanamycin.

The cloning of single-stranded recombinant molecules can optionally be performed by PCR with two initiators of the complete gene and cloning of the double-stranded product of this amplification. To avoid undesirable mutations, this amplification will be performed with polymerase of the Pfu type and with a limited number of cycles.

The plasmids of the clones that are significantly more resistant to kanamycin than the initial stock are purified and used as matrices for PCR with the polymerase Pfu, under high fidelity conditions, with the phosphorylated/nonphosphorylated initiator couple as previously defined. This produces the second generation of single-stranded fragments after a treatment with lambda exonuclease and fragmentation with restriction enzymes. The enzymes used for this step can comprise a different mixture (Bst NI, Taq I and Mnl I).

The recombination and selection steps are repeated several times until a substantial increase in resistance to kanamycin is obtained.

What is claimed is:

1. A ligase-mediated method of recombination, comprising:
   providing oligonucleotide fragments derived from each of at least two heterologous polynucleotide sequences of a polynucleotide bank;
   hybridizing the fragments to an assembly matrix so that the hybridized fragments are oriented for ligation with each other; and
   ligating the hybridized fragments having immediately adjacent ends with a ligase to form random recombinant polynucleotide sequences.

2. The method of claim 1, further comprising at least one repetition of the providing step, the hybridizing step or the ligating step.

3. The method of claim 2, wherein the hybridizing step is repeated, before or after the ligating step, until the ends of more than half of the hybridized fragments are immediately adjacent to each other.

4. The method of claim 3, wherein, before a final ligating step, the ends of all of the hybridized fragments are immediately adjacent to each other.

5. The method of claim 1, wherein any polymerase extension performed during the hybridizing or ligating step, or between the hybridizing and ligating step, consists of gap filling between the hybridized fragments.

6. The method of claim 1, wherein the method is performed without a polymerase.

7. The method of claim 1, wherein the method is performed in vitro.

8. The method of claim 1, wherein, at the providing step, the fragments are cleavage fragments.

9. The method of claim 1, wherein, at the providing step, the fragments are random fragments.

10. The method of claim 1, wherein the method of recombination is a method of random recombination.

11. The method of claim 1, wherein the providing step comprises providing fragments that have been obtained in a manner such that degree of recombination desired and the position of the recombination points have been precisely controlled.

12. The method of claim 1, wherein the providing step comprises fragmenting the at least two heterologous polynucleotide sequences in a manner such that degree of recombination desired and the position of the recombination points have been precisely controlled.

13. The method of claim 1, wherein the at least two heterologous polynucleotide sequences differ from each other at more than one base position.

14. The method of claim 13, wherein the at least two heterologous polynucleotide sequences are derived from at least two distinct genes.

15. The method of claim 14, wherein the at least two heterologous polynucleotide sequences are derived from at least two distinct genes from at least two distinct gene families.

16. The method of claim 14, wherein the at least two heterologous polynucleotide sequences are derived from at least two distinct genes from at least two different species of organism.

17. The method of claim 1, wherein the at least two heterologous polynucleotide sequences are single-stranded.

18. The method of claim 1, wherein at least one assembly matrix is double-stranded and it is first denatured and then added in single-stranded form at the hybridizing step.

19. The method of claim 1, wherein at least one assembly matrix is single-stranded.

20. The method of claim 1, wherein the ligase is a thermostable ligase that is active at temperatures at or above 65° C.

21. The method of claim 1, wherein the polynucleotide bank comprises a variety of polynucleotide sequences obtained by mutagenesis or by combining genes of close or distinct families.

22. The method of claim 1, wherein, in addition to said fragments and assembly matrix, oligonucleotides of varying length, and single- or double-stranded, are added at the providing or hybridizing step.

23. The method of claim 1, wherein the polynucleotide bank comprises a restricted bank.

24. The method of claim 1, wherein the recombinant polynucleotide formed by the method is a non-naturally occurring polynucleotide.

25. The method of claim 1, further comprising cloning the recombinant polynucleotide sequence.

26. The method of claim 1, wherein a fragment from the providing step is used as the assembly matrix.

27. The method of claim 1, wherein the providing step comprises subjecting the at least two heterologous polynucleotide sequences to hydrolysis by the action of a plurality of different restriction enzymes or by the action of one or more restriction enzymes having a large number of cutting sites on the at least two heterologous polynucleotide sequences.

28. The method of claim 27, wherein a fragment obtained at the providing step by a treatment with restriction enzymes is used as the assembly matrix.

29. The method of claim 1, wherein the providing step further comprises randomly fragmenting the at least two heterologous polynucleotide sequences by treating them with DNAase I.

30. The method of claim 29, wherein a fragment produced by the random fragmenting is used as the assembly matrix at the hybridizing step.

31. The method of claim 1, wherein the hybridizing and ligating steps are performed simultaneously.

32. The method of claim 1, wherein the at least two heterologous polynucleotide sequences are double-stranded and the providing step further comprises denaturing the fragments obtained at the providing step.

33. The method of claim 1, further comprising using the recombinant polynucleotide sequence as a source of fragments or as an assembly matrix during at least one repetition of the providing or hybridizing step.

34. The method of claim 1, further comprising separating the recombinant polynucleotide sequence formed at the ligating step from the assembly matrix.

35. The method of claim 34, wherein the recombinant polynucleotide sequence is separated from the assembly matrix using a marker present on the assembly matrix or on the recombinant polynucleotide sequence.

36. The method of claim 1, further comprising, before the selecting step, using polymerase extension to amplify the number of copies of the recombinant polynucleotide sequence.

37. The method of claim 1, wherein the selected recombinant polynucleotide sequence is used to form a new polynucleotide bank for a repeat of one or more of the providing step, the hybridizing step, the ligating step or the selecting step.

38. The method of claim 1, wherein the selection is performed by in vitro expression of the recombinant polynucleotide sequence.

39. The method of claim 1, further comprising using a degrading enzyme at the hybridizing or ligating step that specifically recognizes and degrades any nonhybridized ends of the fragments when said nonhybridized ends overlap hybridized fragments on the assembly matrix.

40. The method of claim 39, wherein the degrading enzyme is Flap endonuclease.

41. The method of claim 39, wherein the degrading enzyme and the ligase are equally thermostable at temperatures at or above 65° C.

42. The method of claim 39, wherein the degrading enzyme is an exonuclease that cleaves single-stranded nucleic acids.

43. A ligase-mediated method of recombination, comprising:
    hybridizing oligonucleotide fragments derived from each of at least two heterologous polynucleotide sequences to an assembly matrix so that the hybridized fragments are oriented for ligation with each other; and
    ligating the hybridized fragments having immediately adjacent ends with a ligase to form random recombinant polynucleotide sequences.

44. The method of claim 1, wherein the recombinant polynucleotide sequences comprise at least two recombinant polynucleotide sequences.

* * * * *